US007097629B2

(12) United States Patent
Blair

(10) Patent No.: US 7,097,629 B2
(45) Date of Patent: Aug. 29, 2006

(54) MULTI-LAYERED SEALED SWAB

(75) Inventor: Paul Blair, Jonesboro, GA (US)

(73) Assignee: Illinois Tool Works Inc., Glenview, IL (US)

( * ) Notice: Subject to any disclaimer, the term of this patent is extended or adjusted under 35 U.S.C. 154(b) by 321 days.

(21) Appl. No.: 10/428,619

(22) Filed: May 2, 2003

(65) Prior Publication Data

US 2004/0220507 A1 Nov. 4, 2004

(51) Int. Cl.
*A61M 35/00* (2006.01)

(52) U.S. Cl. ........................... 604/1; 604/289; 15/222; 15/244.1; 15/244.3

(58) Field of Classification Search ................ 604/1-3, 604/289, 310; 606/162, 190; 15/209.1, 15/217, 222, 228, 244.1, 244.2, 244.3, 244.4; 600/575, 576, 362; 602/41-79

See application file for complete search history.

(56) References Cited

U.S. PATENT DOCUMENTS 1,909,967 A * 5/1933 Jones ............................ 604/1
3,376,595 A * 4/1968 Cole ........................... 15/228
3,393,963 A * 7/1968 Nadai ......................... 401/207
3,542,025 A * 11/1970 Gustafson ...................... 604/1
3,586,380 A * 6/1971 Alibeckoff ................... 300/21
3,591,885 A 7/1971 Fritzen, Jr. et al.
3,818,911 A * 6/1974 Fournier ........................ 604/1
4,291,697 A * 9/1981 Georgevich ..................... 604/3
4,430,013 A * 2/1984 Kaufman .................... 401/132
4,718,889 A * 1/1988 Blasius et al. ................. 604/1
4,795,421 A * 1/1989 Blasius et al. ................. 604/1
4,820,579 A * 4/1989 Aszman ................... 428/304.4
4,953,560 A * 9/1990 Samuels ..................... 600/572
5,094,559 A * 3/1992 Rivera et al. ............... 401/132
5,291,887 A * 3/1994 Stanley et al. .............. 600/573
5,511,654 A * 4/1996 de la Rocha ............. 206/15.3
5,596,787 A * 1/1997 Stevens et al. ............ 15/220.1
5,738,643 A * 4/1998 Stredic, III .................... 604/1
5,806,128 A * 9/1998 Love ......................... 15/209.1
5,817,121 A * 10/1998 Christoudias ............... 606/190
5,947,986 A * 9/1999 Lewis ........................ 606/161
5,991,960 A * 11/1999 Johnson ..................... 15/210.1
D428,225 S * 7/2000 Prime et al. ................. D32/40
6,101,661 A * 8/2000 Policicchio et al. .......... 15/228
6,258,045 B1 * 7/2001 Ray et al. ................... 600/573
6,298,517 B1 * 10/2001 McKay ........................ 15/228
2003/0041469 A1 * 3/2003 Turtzo ........................... 34/89
2003/0107195 A1 * 6/2003 Zambanini et al. ...... 280/47.34
2003/0181933 A1 * 9/2003 Eicoff .......................... 606/162
2004/0267180 A1 * 12/2004 Beaudry ........................ 604/1

FOREIGN PATENT DOCUMENTS

EP 1 473 092 A1 * 11/2004

* cited by examiner

*Primary Examiner*—Tatyana Zalukaeva
*Assistant Examiner*—Michael G. Bogart
(74) *Attorney, Agent, or Firm*—Mark W. Cross, Esq.; Donald J. Breh, Esq.; Levenfeld Pearlstein, LLC

(57) ABSTRACT

A cleaning swab is for wet or dry use. The swab includes an elongated handle defining a longitudinal axis. The handle has a cleaning head end and a grasping end. The swab includes a multi layer cleaning head having a core, a mid-layer and an outer layer. The core and the mid-layer are absorbent. The outer layer is formed from a cleaning textile. The outer layer is sealed to itself and to the handle to isolate the core and mid-layer.

15 Claims, 1 Drawing Sheet

MULTI-LAYERED SEALED SWAB

BACKGROUND OF THE INVENTION

The present invention is directed to a swab for cleaning. More particularly, the present invention pertains to a multi-layer swab having a sealed outer layer or cover.

Swabs are used in all manners of cleaning. For example, everyone will recognize common cotton tipped swabs that are used for person hygiene and care. Because of the compact and effective nature of these swabs, they have been adopted for use in numerous areas of technology and manufacture. One such area is the manufacture of advanced optical components for use in aerospace and navigation systems.

During manufacture and use of optical components it is not unusual for pieces of manufacturing debris, such as dust and fibers or other particulate debris to be left on surface of the components. It is also not unusual for light oils, such as fingerprint and other natural skin oils to be found on many of these parts. The debris and oils can significantly degrade, distort or prevent the proper and precise transmission of images.

Numerous types of cleaning implements have been used, with some degrees of success, to clean these particularly sensitive areas. It has, however, been observed that cleaning implements formed from non-particulate removing materials may not be acceptable for this use. Specifically, it has been found that particulates that are not removed can become lodged in and around these components, thus adversely effecting the quality of the images.

Often, liquids are used to assist in the cleaning process. For example, water or other light solvents maybe applied to the swab to assist in removing contaminants such as oils, particulates and the like.

Other cleaning swabs have also been used with varying degrees of success. For example, one known swab includes a polyurethane foam over a cotton core. However, it has been found that polyurethane is not sufficiently soft (for contact with sensitive components and surfaces), and is not sufficiently hydrophilic (to absorb water or other solvents) to facilitate the cleaning process.

Accordingly, there exists a need for a swab-type cleaning device that can be used for cleaning sensitive components and surfaces. Desirably, such a device leaves little to no residue from the device within the component or on the surface. More desirably, such a device can be used wet or dry; that is, it can be used with or without a solvent (such as water) to facilitate cleaning. Most desirably, such a cleaning device is structurally stable when wet, serves well to distribute any liquid throughout the device and is resistant to cutting.

BRIEF SUMMARY OF THE INVENTION

A cleaning swab is for wet or dry use. The swab includes an elongated handle and a multi layer cleaning head. The swab can be used for cleaning sensitive components and surfaces such as those found in advanced optical equipment. The swab leaves little to no residue (from the swab) within the component or on the surface. Such a swab is structurally stable when wet and serves well to distribute any liquid throughout the swab cleaning head.

The multi layer cleaning head has a core, a mid-layer and an outer layer. The core and the mid-layer are formed from absorbent materials. In a present embodiment, the core is formed from cotton and the mid-layer is formed from a foam, such as a polyurethane foam.

The outer layer is formed from a cleaning textile, such as polyvinyl acetate (PVA) or a micro denier cleaning fabric. Preferably, the outer layer is sealed to itself and to the handle to isolate the core and mid-layer to, for example, prevent the egress of particulate and fibers from the core and mid-layer. The outer layer can be sealed by, for example, heat sealing to itself and to the handle.

The handle can be formed from wood or a plastic material, preferably one that is static dissipative.

These and other features and advantages of the present invention will be apparent from the following detailed description, in conjunction with the appended claims.

BRIEF DESCRIPTION OF THE SEVERAL VIEWS OF THE DRAWINGS

The benefits and advantages of the present invention will become more readily apparent to those of ordinary skill in the relevant art after reviewing the following detailed description and accompanying drawings, wherein.

DETAILED DESCRIPTION OF THE INVENTION

Figure 1:
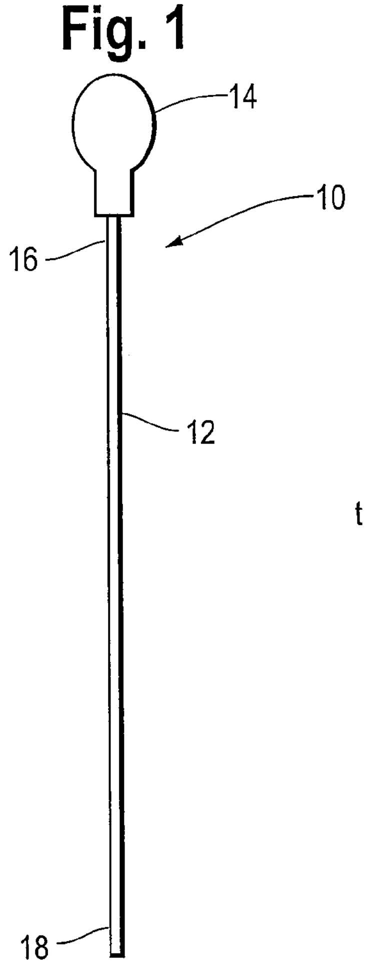
FIG. 1 illustrates a multi-layer sealed swab embodying the principles of the present invention.

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiment illustrated.

It should be further understood that the title of this section of this specification, namely, "Detailed Description Of The Invention", relates to a requirement of the United States Patent Office, and does not imply, nor should be inferred to limit the subject matter disclosed herein.

Figure 2:
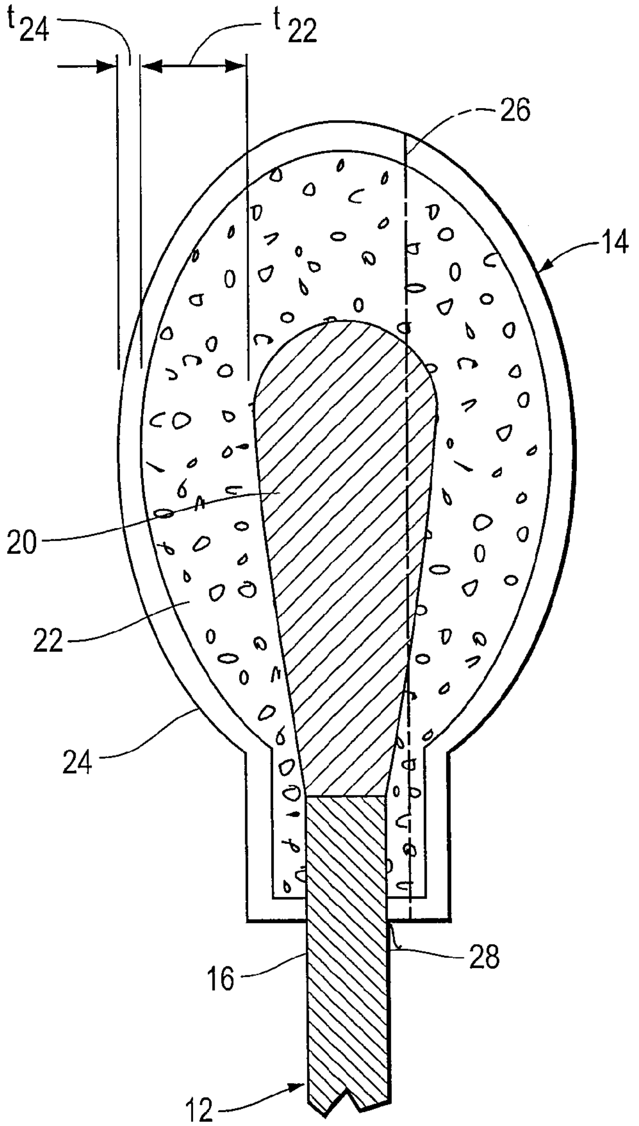
FIG. 2 is an enlarged, cross-sectional view of the swab head.

Referring to the figures and in particular to FIG. 1 there is shown a multi-layer sealed swab 10 in accordance with the principles of the present invention. The swab 10 includes a handle 12 and a cleaning head 14. The cleaning head 14 is formed in a multi-layered construction as best seen in FIG. 2. The present swab 10 can be used for cleaning sensitive components and surfaces such as those used in fiber optics and other telecommunications equipment. A swab 10 in accordance with the present invention leaves little to no residue (e.g., fibers) from the device within the component or on the surface, and can be used wet or dry (i.e., with or without a solvent) to facilitate cleaning. The swab 10 has been found to be structurally stable when wet and serves well to distribute any liquid (e.g., solvent) throughout the cleaning head 14 for cleaning.

In a present embodiment, the handle 12 is formed from a wood or polymeric material, such as polypropylene or the like formed in an injection or extrusion molding process. The handle 12 can also be formed as a plastic alloy or a filled plastic to provide enhanced static dissipative properties. The handle has first and second or cleaning and grasping ends, 16, 18, respectively.

The cleaning head 14 is formed in a multi layer construction. In one embodiment, the head 14 includes a core 20 formed from a bud of cotton. The core 20 is covered with a middle layer 22 (also referred to as a mid-layer) of hydrophilic material, such as an open-cell polyurethane foam. In a present embodiment, the mid-layer 22 is a 100 ppi open-cell polyurethane foam.

The hydrophilic mid-layer 22 is then covered with an outer layer 24 of a cut resistant material. Preferably, the outer layer 24 is a cleaning fabric or textile. One outer layer 24 material is a layer of polyvinyl acetate (PVA) foam. Alternately, the outer layer 24 is formed from a polyester, micro denier or other suitable cleaning textile or fabric.

The outer layer 24 is sealed or seamed to itself (as indicated at 26) so as to fully enclose the middle layer 22 and core 20. Preferably, the outer layer 24 is also sealed or welded to the handle 12 (as indicated at 28) to essentially isolate the middle layer 22 and core 20. Sealing the outer layer 24 onto itself (as at seam 26), as well as at the handle 12, serves to fully isolate the mid-layer 22 and core 20 to prevent the egress of fibers or other particulate matter from the mid-layer 22 and core 20.

In a present swab 10, the mid-layer 22 has a thickness $t_{22}$ of about 5.0 mm and the outer layer 24 has a thickness $t_{24}$ of about 1.0 mm. The thicknesses of the various layers can vary depending upon the specific desired application or use for the swab 10.

In an alternate construction (not shown), the core and middle layer can be combined into a single core portion formed from, for example, polyurethane foam. The polyurethane foam can be bonded directly to the handle by welding or ultrasonic techniques to melt the foam and handle together.

It is anticipated that the swab head or cleaning head 14 will be formed in various sizes and shapes for a variety of specific cleaning tasks. The cleaning head 14 can be formed in an oval or ovate shape, it can be formed in a rectangular shape, or any other shape as needed for a particular application.

It has been found that the present novel swab 10 construction provides a number of advantages over known swabs. First, the outer layer 24, being sealed or seamed (as by, for example, heat) provides a neat and soft sealed seam 26. This is in contrast to known PVA swabs which are wrapped over cotton or are simply glued to handles.

In addition, the polyurethane foam mid-layer 22 beneath the outer layer 24 provides a number of enhanced cleaning features. First, the mid-layer 22 provides structural stability to the outer layer 24. Those skilled in the art will recognize that when the outer layer 24 (e.g., PVA) becomes wet with water, it can absorb an enormous times its weight in water. As such the outer layer 24 can become structurally unstable, sagging and possibly tearing under its own weight (with the absorbed water).

It has been found that the polyurethane mid-layer 22 beneath the outer layer 24 distributes the weight of the water more evenly and supports the weight more effectively. As such, the present swab 10 has considerably more structural integrity than known swabs.

The polyurethane foam mid-layer 22 further serves to store additional solvent (e.g., water) to maintain the outer layer 24 wet. That is, the polyurethane foam mid-layer 22 essentially serves as a reservoir to store water for use and absorption by the outer layer 24 for cleaning.

Moreover the polyurethane foam mid-layer 22 protects the cotton core 20 when the swab 10 is used around sharp edges. It has been found that the present construction, when used to clean surface mirrors and advanced optics that may have sharp edges, prevents cutting through the outer layer 24 and possible subsequent release of fibers from the cotton core 20. As such, no fibers are released by the present swab 10 that could otherwise contaminate the surfaces and components of sensitive fiber optic equipment.

It has also been found that the present swab 10 is sufficiently flexible to conform to the shape of the surfaces being cleaned, while at the same time it is sufficiently resilient to retain its shape. This combination or balance of resiliency and flexibility provides enhanced cleaning characteristics when compared to known swabs.

Importantly, it has also been found that when used with a cleaning textile outer layer 24 (such as PVA or micro denier), excellent cleaning and contamination removal characteristics have been shown. Micro denier and PVA have been shown to exhibit superior cleaning abilities, particularly with respect to the removal of contaminants, when compared to other materials, such as foam. In combination with the foam, however, it has been found that the outer layer 24 cleaning ability is enhanced by the ability of the mid-layer 22 and core 20 to provide a sufficient reserve or reservoir of cleaning solution. It has also been found that the foam mid-layer 22 provides a sufficient cushion to moderate the pressure applied during cleaning, as well as (as set forth above) conformance to the shape of the surface being cleaned.

Advantageously, the present swab 10, unlike known polyurethane foam over cotton core swabs, provides a soft, hydrophilic cleaning implement. Moreover, the unique combination of the cleaning material outer layer 24 foam mid-layer 22 offers a balance between softness (for conformance to the surface of the article being cleaned) and stiffness (to assure good contact and complete cleaning), while at the same time providing absorption for retaining solvents such as water to facilitate the cleaning process.

All patents referred to herein, are hereby incorporated herein by reference, whether or not specifically done so within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

What is claimed is:

1. A cleaning swab for wet or dry use, comprising:
- a handle defining a longitudinal axis, the handle being elongated and having a cleaning head end and a grasping end; and
- a multi layer cleaning head, rigidly and non-removably affixed to the handle so as to enclose a portion of the handle, the head having a core a mid-layer and an outer layer, the core and the mid-layer being absorbent and the outer layer being formed from a cleaning textile, wherein the outer layer is sealed to itself and to the handle to isolate the care and mid-layer.

2. A cleaning swab for wet or dry use, comprising:
- a handle defining a longitudinal axis, the handle being elongated and having a cleaning head end and a grasping end; and
- a multi layer cleaning head rigidity and non-removably affixed to the handle, the cleaning head having a core a mid-layer and an outer layer, the core and the mid-layer being absorbent and the outer layer being formed from a cleaning textile, wherein the outer layer is a polyvinyl acetate (PVA) material sealed to itself and to the handle so as to enclose a portion of the handle and to isolate the core and mid-layer.

3. A cleaning swab for wet or dry use, comprising:

a handle defining a longitudinal axis, the handle being elongated and having a cleaning head end and a grasping end; and a multi layer cleaning head, rigidly and non-removably affixed to the handle, the cleaning head having a core a mid-layer and an outer layer, the core and the mid-layer being absorbent and the outer layer being formed from a cleaning textile, wherein the outer layer is a micro denier material scaled to itself and to the handle, so as to enclose a portion of the handle and to isolate the core and mid-layer.

4. The cleaning swab in accordance with claim 1 wherein the core is cotton.

5. The cleaning swab in accordance with claim 1 wherein the mid-layer is a foam.

6. The cleaning swab in accordance with claim 5 wherein the foam is a polyurethane foam.

7. The cleaning swab in accordance with claim 6 wherein the foam is a 100 ppi foam material.

8. A cleaning swab for wet or dry use, comprising:

a handle defining a longitudinal axis, the handle being elongated and having a cleaning head end and a grasping end; and a multi layer cleaning head, rigidly and non-removably affixed to the handle, the cleaning head having a core a mid-layer and an outer layer, the care and the mid-layer being absorbent and the outer layer being formed from a cleaning textile, wherein the outer layer is a heat sealed to itself and to the handle so as to enclose a portion of the handle and to isolate the core and mid-layer.

9. The cleaning swab in accordance with claim 1 wherein the handle is wood.

10. The cleaning swab in accordance with claim 1 wherein the handle is a plastic material.

11. The cleaning swab in accordance with claim 10 wherein the plastic material is a static dissipative material.

12. A cleaning swab for wet or dry use, comprising:

a handle defining a longitudinal axis, the handle being elongated and having a cleaning head end and a grasping end; and a multi layer cleaning head, rigidly and non-removably affixed to the handle, the cleaning head having a cotton core a mid-layer of polyurethane foam and an outer layer of a PVA or micro denier material, the core and the mid-layer being absorbent and the outer layer being sealed to itself and to the handle, so as to enclose a portion of the handle and to isolate the cotton core and polyurethane foam mid-layer.

13. The cleaning swab in accordance with claim 12 wherein the polyurethane foam is a 100 ppi foam material.

14. The cleaning swab in accordance with claim 12 wherein the handle is a plastic material.

15. The cleaning swab in accordance with claim 14 wherein the plastic material is a static dissipative material.

* * * * *

UNITED STATES PATENT AND TRADEMARK OFFICE

CERTIFICATE OF CORRECTION

PATENT NO. : 7,097,629 B2
APPLICATION NO. : 10/428619
DATED : August 29, 2006
INVENTOR(S) : Paul Blair It is certified that error appears in the above-identified patent and that said Letters Patent is hereby corrected as shown below:

Claim 8, line 67 should read:

"mid-layer and an outer layer, the core and the mid-layer"

Signed and Sealed this

Twenty-first Day of November, 2006

JON W. DUDAS
*Director of the United States Patent and Trademark Office*